(12) United States Patent
Liao et al.

(10) Patent No.: US 11,117,853 B2
(45) Date of Patent: Sep. 14, 2021

(54) METHODS FOR MANUFACTURING AND DECOLORIZING DIOCTYL TEREPHTHALATE

(71) Applicant: NAN YA PLASTICS CORPORATION, Taipei (TW)

(72) Inventors: Te-Chao Liao, Taipei (TW); Jung-Jen Chuang, Taipei (TW); Chung-Yu Chen, Taipei (TW); Che-Jung Hsu, Taipei (TW)

(73) Assignee: NAN YA PLASTICS CORPORATION, Taipei (TW)

( * ) Notice: Subject to any disclaimer, the term of this patent is extended or adjusted under 35 U.S.C. 154(b) by 0 days.

(21) Appl. No.: 17/002,930

(22) Filed: Aug. 26, 2020

(65) Prior Publication Data
US 2021/0122699 A1    Apr. 29, 2021

(30) Foreign Application Priority Data
Oct. 28, 2019    (TW) .................. 108138748

(51) Int. Cl.
  *C07C 67/56*    (2006.01)
  *C07C 67/08*    (2006.01)
  (Continued)

(52) U.S. Cl.
  CPC .............. *C07C 67/56* (2013.01); *C07C 67/08* (2013.01); *C07C 67/54* (2013.01); *C07C 67/60* (2013.01);
  (Continued)

(58) Field of Classification Search
  CPC ......... C07C 67/08; C07C 67/56; C07C 67/60; C07C 67/62; C07C 67/54; C07C 69/82
  See application file for complete search history.

(56) References Cited

U.S. PATENT DOCUMENTS 5,101,064 A * 3/1992 Dupont .................. C07C 67/03
560/78

FOREIGN PATENT DOCUMENTS

| CN | 102010337 A | 4/2011 |
| CN | 102701984 A | 10/2012 |

(Continued)

OTHER PUBLICATIONS

CN 102241592, Yinzhang, Z. et al., Method for producing dioctyl terephthalate from polyester waste, English translation, 6 pages (Year: 2011).*

(Continued)

*Primary Examiner* — Yate' K Cutliff
(74) *Attorney, Agent, or Firm* — Li & Cai Intellectual Property (USA) Office

(57) ABSTRACT

A method for manufacturing and a method for decolorizing dioctyl terephthalate are provided. The decolorizing dioctyl terephthalate includes: providing an unpurified dioctyl terephthalate; mixing the unpurified dioctyl terephthalate with a reducing agent and an adsorption medium to obtain a first decolorizing product; and mixing the first decolorizing product with a decolorizing adsorbent material to obtain a second decolorizing product. The method for manufacturing dioctyl terephthalate includes: a transesterification step, an alkaline washing and neutralization step, a redox step, a decolorization step and a stripping step; the decolorizing adsorbent material has an acid value between 0.1 and 2 mg KOH/g, a relative humidity between 2 and 10%, and a fineness between 80 and 100 $cm^2$/g.

10 Claims, 1 Drawing Sheet

(51) Int. Cl.
*C07C 69/82* (2006.01)
*C07C 67/62* (2006.01)
*C07C 67/60* (2006.01)
*C07C 67/54* (2006.01)
C07C 67/03 (2006.01)

(52) U.S. Cl.
CPC .............. *C07C 67/62* (2013.01); *C07C 69/82* (2013.01); C07C 67/03 (2013.01)

(56) References Cited

FOREIGN PATENT DOCUMENTS

| | | | | | |
|---|---|---|---|---|---|
| CN | 104230714 A | | 12/2014 | | |
| CN | 106995371 | * | 8/2017 | ............. | C07C 67/08 |
| CN | 106995371 A | | 8/2017 | | |
| CN | 107216250 | * | 9/2017 | ............. | C07C 67/03 |
| CN | 109809988 A | | 5/2019 | | |
| CN | 102241592 | * | 11/2020 | ............. | C07C 69/82 |

OTHER PUBLICATIONS

CN 106995371, Huang, S, Process for separation of dioctyl terephthalate, English translation, 7 pages (Year: 2017).*
CN 107216250, Wang, L., Method for preparing dioctyl terephthalate by using polyethylene terephthalate waste, English translaiton 15 pages (Year: 2017).*

* cited by examiner

METHODS FOR MANUFACTURING AND DECOLORIZING DIOCTYL TEREPHTHALATE

CROSS-REFERENCE TO RELATED PATENT APPLICATION

This application claims the benefit of priority to Taiwan Patent Application No. 108138748, filed on Oct. 28, 2019. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to methods for manufacturing and decolorizing dioctyl terephthalate, and more particularly to methods for manufacturing and decolorizing dioctyl terephthalate plasticizer from recycled polyethylene terephthalate.

BACKGROUND OF THE DISCLOSURE

Plasticizers are widely used in the processing of polymers, such as synthetic rubber, plastics, and coatings. The purpose of the plasticizer is to increase the plasticity, fluidity, and provide flexibility to the finished products, so that the plasticizers are essential additives for the polymer industry. Dioctyl terephthalate (DOTP) is a non-toxic and environmentally friendly non-phthalate plasticizer. Compared with the conventional dioctyl phthalate (DOP) that is commonly used, dioctyl terephthalate has the advantages of heat resistance, cold resistance, low volatility, extraction resistance, flexibility, and good electrical insulation performance.

In addition, dioctyl terephthalate has low volatility and high plasticization efficiency, so that it is widely used in rubbers such as nitrile rubber, neoprene rubber, ternary butadiene rubber, and products such as wire, cable, rubber, tape, gloves, shoes, etc.

Generally, the manufacturing method of dioctyl terephthalate is based on the direct esterification reaction of terephthalic acid (TPA) and octanol; however, the cost of terephthalic acid is relatively high, which leads to higher production costs.

Polyethylene terephthalate (polyethylene terephthalate, PET) is the material among thermoplastic polyesters with the largest output and the lowest cost. In recent years, the production of dioctyl terephthalate from the recycling of polyethylene terephthalate (PET) with octanol has led to significant cost advantages. However, the process of recycled polyethylene terephthalate will produce some by-products, resulting in the product being dark brown in color, which fails to meet the requirements of industrial applications. In order to overcome the aforementioned defects, how the manufacturing method can be improved, thus increasing the decoloring effect of dioctyl terephthalate, has become one of the most important challenges in the industry that needs to be solved.

SUMMARY OF THE DISCLOSURE

In response to the above-referenced technical inadequacies, the present disclosure provides methods for manufacturing and decolorizing dioctyl terephthalate plasticizer from recycled polyethylene terephthalate.

In one aspect, the present disclosure provides a method for decolorizing dioctyl terephthalate, comprising: providing an unpurified dioctyl terephthalate; mixing the unpurified dioctyl terephthalate with a reducing agent and an adsorption medium, stirring for 1.5 to 3 hours, keeping for 6 to 10 hours, and filtering out the liquid, to obtain a first decolorizing product; and mixing the first decolorizing product with a decolorizing adsorbent material, stirring for 1.5 to 3 hours, keeping for 6 to 10 hours, and filtering out the liquid, to obtain a second decolorizing product; wherein the decolorizing adsorbent material has an acid value between 0.1 and 2 mg KOH/g, a relative humidity between 2 and 10%, and a fineness between 80 and 100 $cm^2/g$.

In certain embodiments, the reducing agent is at least one selected from the group consisting of thiourea dioxide aqueous solution, hydrogen peroxide, and an aqueous solution of sodium borohydride and sodium hydroxide.

In certain embodiments, the adsorption medium is at least one selected from the group consisting of activated carbon, zeolite, molecular sieve, diatomaceous earth, acid clay, activated clay, or activated alumina.

In another aspect, the present disclosure provides a method for manufacturing dioctyl terephthalate, including: a transesterification step, an alkaline washing and neutralization step, a redox reaction step, a decolorization step and a stripping step; in which, the transesterification step: mixing a recycled polyethylene terephthalate and a C3-C12 alcohol in a weight ratio of 1:0.8 to 1.5 with a catalyst, to obtain a slurry of dioctyl terephthalate; wherein, the slurry of dioctyl terephthalate includes an unpurified dioctyl terephthalate and an ethylene glycol; the alkaline washing and neutralization step: neutralizing the unpurified dioctyl terephthalate with an alkali hydroxides solution; the redox reaction step: mixing the unpurified dioctyl terephthalate with a reducing agent and an adsorption medium, stirring for 1.5 to 3 hours, keeping for 6 to 10 hours, and filtering out the liquid, to obtain a first decolorizing product; the decolorization step: mixing the first decolorizing product with a decolorizing adsorbent material, stirring for 1.5 to 3 hours, keeping for 6 to 10 hours, and filtering out the liquid, to obtain a second decolorizing product; and the stripping step: stripping the second decolorizing product with steam at 100° C. to 200° C. for 2 hours to obtain a decolorized dioctyl terephthalate; wherein, the decolorizing adsorbent material has an acid value between 0.1 and 2 mg KOH/g, a relative humidity between 2 and 10%, and a fineness between 80 and 100 $cm^2/g$.

In certain embodiments, the transesterification step is under a reaction pressure between −30 and 1013 mbar, a reaction temperature between 200 and 250° C., and a reaction time between 2 and 3 hours.

In certain embodiments, the C3-C12 alcohol is at least one selected from the group consisting of N-propanol, isopropanol, n-butanol, sec-butanol, tert-butanol, pentanol, hexanol, heptanol, octanol, isooctanol, 2-ethylhexanol, ethylene glycol monomethyl ether, ethylene glycol monoethyl ether and ethylene glycol monobutyl ether.

In certain embodiments, the catalyst is at least one selected from the group consisting of tetraisopropyl titanate, tetraisobutyl titanate and tetra (2-ethylhexyl) titanate.

In certain embodiments, the alkali hydroxides solution includes: 5 to 20 wt % hydroxide based on a total amount of the alkali hydroxides solution.

In certain embodiments, the reducing agent is at least one selected from the group consisting of thiourea dioxide aqueous solution, hydrogen peroxide, and an aqueous solution of sodium borohydride and sodium hydroxide.

In certain embodiments, the adsorption medium is at least one selected from the group consisting of activated carbon, zeolite, molecular sieve, diatomaceous earth, acid clay, activated clay, or activated alumina.

Therefore, by virtue of "mixing the unpurified dioctyl terephthalate with a reducing agent and an adsorption medium, stirring for 1.5 to 3 hours, keeping for 6 to 10 hours, and filtering out the liquid, to obtain a first decolorizing product", "mixing the first decolorizing product with a decolorizing adsorbent material, stirring for 1.5 to 3 hours, keeping for 6 to 10 hours, and filtering out the liquid, to obtain a second decolorizing product", and "wherein the decolorizing adsorbent material has an acid value between 0.1 and 2 mg KOH/g, an relative humidity is between 2 and 10%, and a fineness between 80 and 100 $cm^2/g$", the method for manufacturing and decolorizing dioctyl terephthalate of the present disclosure improves the decoloring effect of dioctyl terephthalate.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
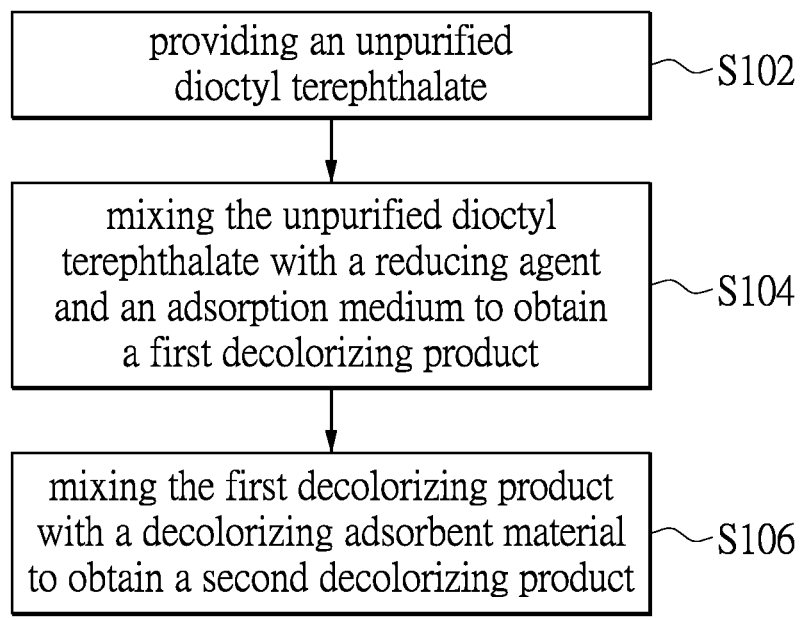
FIG. 1 is a flowchart of a method for decolorizing dioctyl terephthalate according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

Referring to FIG. 1, a first embodiment of the present disclosure provides a method for decolorizing dioctyl terephthalate, including S102: providing an unpurified dioctyl terephthalate; S104: mixing the unpurified dioctyl terephthalate with a reducing agent and an adsorption medium to obtain a first decolorizing product; and S106: mixing the first decolorizing product with a decolorizing adsorbent material to obtain a second decolorizing product.

In step 102, the source of unpurified dioctyl terephthalate is not limited. Generally, the main method for manufacturing dioctyl terephthalate is an esterification method and a transesterification method. The esterification method is made by directly esterifying terephthalic acid (TPA) and octanol in the presence of a catalyst. The transesterification method is a transesterification reaction between dimethyl terephthalate (DMT) or polyethylene terephthalate waste and octanol in the presence of the catalyst. After the reaction, the unpurified dioctyl terephthalate is detected by a platinum-cobalt colorimetry to be approximately #200 to #500.

The principle of platinum-cobalt (Pt—Co) colorimetry is to prepare a color standard solution of potassium chloroplatinate and cobalt chloride, and compare the color with a water sample (visual comparison with a tested sample to determine the color intensity of the sample), the color of 1 mg platinum and 0.5 mg cobalt per liter of water is called 1 degree, which is the standard color unit, that is, color chromaticity.

Step S104 after mixing the unpurified dioctyl terephthalate with the reducing agent and the adsorption medium, stirring for 1.5 to 3 hours, and keeping for 6 to 10 hours, and filtering out the liquid, to obtain a first decolorizing product.

Specifically, the reducing agent is at least one selected from the group consisting of thiourea dioxide aqueous solution, hydrogen peroxide, and an aqueous solution of sodium borohydride and sodium hydroxide. The adsorption medium is at least one selected from the group consisting of activated carbon, zeolite, molecular sieve, diatomaceous earth, acid clay, activated clay, or activated alumina. Preferably, the adsorption medium is activated carbon, the activated carbon may be selected from coal-based activated carbon, pitch-based activated carbon, wood-based activated carbon or coconut shell-based activated carbon. For example, an aqueous solution of thiourea dioxide with activated carbon and 50% hydrogen peroxide with activated carbon can be used. However, the present disclosure is not limited therefore.

Step S106 after mixing the first decolorizing product with the decolorizing adsorbent material, stirring for 1.5 to 3 hours, and keeping for 6 to 10 hours, filtering out the liquid, to obtain a second decolorizing product.

In detail, the decolorizing adsorbent material has an acid value between 0.1 and 2 mg KOH/g, a relative humidity between 2 and 10%, and a fineness between 80 and 100 $cm^2/g$. Specifically, the amount of the decolorizing adsorbent material is between 0.1 to 10 wt % based on a total amount of the first decolorizing product, more preferably, the amount of the decolorizing adsorbent material is between 0.1 to 10 wt %, 0.1 to 9 wt %, 0.1 to 8 wt %, 0.1 to 7 wt %, 0.1 to 6 wt %, 0.1 to 5 wt %, 1 to 10 wt %, 2 to 10 wt %, 3 to 10 wt %, 3 to 10 wt %, 4 to 10 wt %, 5 to 10 wt %, 6 to 10 wt %, 7 to 10 wt %, 8 to 10 wt %, or 9 to 10 wt % based on a total amount of the first decolorizing product.

The decolorizing adsorbent material is a nano size level adsorbent material, which can adsorb smaller substances and more pigments than activated carbon, and the decolorizing adsorbent material can be reused after activation and regeneration. For example, the decolorizing adsorbent material can be selected from AMC Co. SUPER JUMBO B acid clay, KingYu Chemical Co. CL001 acid clay, and Toshin Kasei Co., Ltd. Nikkanite S-200 acid clay.

Figure 2:
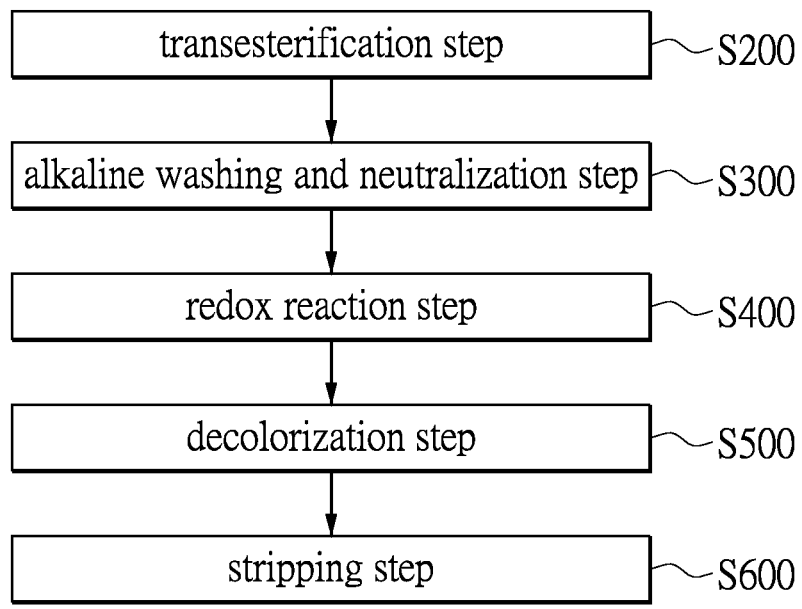
FIG. 2 is a flowchart of a method for manufacturing dioctyl terephthalate according to the first embodiment of the present disclosure.

Referring to FIG. 2, the present disclosure further provides a method for manufacturing dioctyl terephthalate, including S200 transesterification step, S300 alkaline washing and neutralization step, S400 redox reaction step, S500 decolorization step and S600 stripping step.

The S200 transesterification step is to mix a recycled polyethylene terephthalate and a C3-C12 alcohol in a weight ratio of 1:0.8 to 1.5 in the presence of the catalyst, to obtain a slurry of dioctyl terephthalate; in which, the slurry of dioctyl terephthalate includes an unpurified dioctyl terephthalate and an ethylene glycol. After the reaction, the unpurified dioctyl terephthalate is tested by the platinum-cobalt colorimetry to be approximately #200 to #500.

More specifically, the S200 transesterification step can be performed with a high temperature and high pressure reactor, the reaction pressure is between −30 to 1013 mbar, the reaction temperature is between 200 and 250° C., and the reaction time is between 2 and 3 hours. The catalyst is at least one selected from the group consisting of tetraisopropyl titanate, tetraisobutyl titanate and tetra (2-ethylhexyl) titanate.

Polyethylene terephthalate (PET) is a saturated polymer compound formed by polycondensation of terephthalic acid (PTA) or dimethyl terephthalate (DMT) with ethylene glycol. Polyethylene terephthalate is widely used in fiber, beverage bottles, and other fields. Preferably, the recycled polyethylene terephthalate of the present disclosure may be general PET plastic waste, and may be in any individual forms of solid particles, lumps, filaments, cloths, or a mixture of several forms combined, but not limited, therefore. The recycled polyethylene terephthalate can be pretreated by rinsing with deionized water, dry at 45 to 65° C. in an oven for at least 6 hours, or vacuum dry at 140° C. for 12 hours. The dry recycled polyethylene terephthalate is then ground into 2 to 4 mm particles by a pulverizer.

Further, the C3-C12 alcohol is at least one selected from the group consisting of N-propanol, isopropanol, n-butanol, sec-butanol, tert-butanol, pentanol, hexanol, heptanol, octanol, isooctanol, 2-ethylhexanol, ethylene glycol monomethyl ether, ethylene glycol monoethyl ether, and ethylene glycol monobutyl ether. Preferably, the C3-C12 alcohol is isooctanol, and the chemical reaction formula of the present disclosure is as follows:

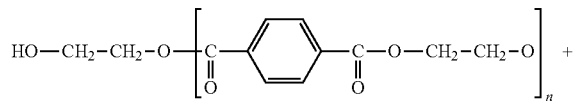

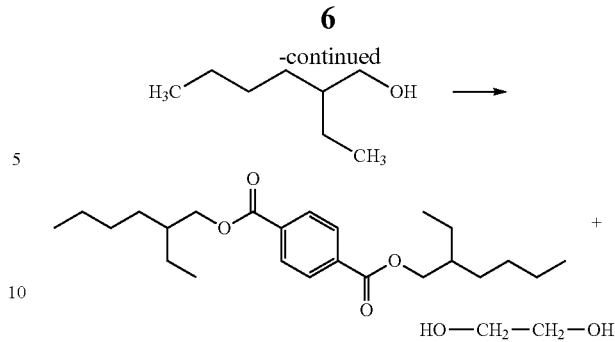

In the S300 alkaline washing and neutralization step, the unpurified dioctyl terephthalate is neutralized with an alkali hydroxides solution. The alkali hydroxides solution includes: 5 to 20 wt % hydroxide based on a total amount of the alkali hydroxides solution. For example, sodium carbonate solution. Optionally, the alkaline washing and neutralization step includes stirring for 0.5 to 5 hours repeatedly for 2 to 5 times, and allowing to stand for 1 to 24 hours to be stratified, then a removal of the alkali hydroxides solution is performed. After the S300 alkaline washing and neutralization step, the colorimetry of unpurified dioctyl terephthalate has decreased from the original #200 to #100-110.

In the S400 redox reaction step: mixing the unpurified dioctyl terephthalate with the reducing agent and the adsorption medium, stirring for 1.5 to 3 hours, keeping for 6 to 10 hours, and filtering out the liquid, to obtain the first decolorizing product.

More specifically, the reducing agent is at least one selected from the group consisting of thiourea dioxide aqueous solution, hydrogen peroxide, and an aqueous solution of sodium borohydride and sodium hydroxide. The adsorption medium is at least one selected from the group consisting of activated carbon, zeolite, molecular sieve, diatomaceous earth, activated clay, or activated alumina Preferably, the adsorption medium is activated carbon, the activated carbon may be selected from coal-based activated carbon, pitch-based activated carbon, wood-based activated carbon or coconut shell-based activated carbon. For example, an aqueous solution of thiourea dioxide with activated carbon, and 50% hydrogen peroxide with activated carbon can be used. However, the present disclosure is not limited therefore.

In the S500 decolorization step: mixing the first decolorizing product with the decolorizing adsorbent material, stirring for 1.5 to 3 hours, keeping for 6 to 10 hours, and filtering out the liquid, to obtain the second decolorizing product.

More specifically, the decolorizing adsorbent material has an acid value between 0.1 and 2 mg KOH/g, a relative humidity between 2 and 10%, and a fineness between 80 and 100 cm$^2$/g. Specifically, the decolorizing adsorbent material is between 0.1 to 10 wt % based on a total amount of the first decolorizing product, more preferably, the decolorizing adsorbent material is a nano size level adsorbent material, which can adsorb smaller substances and more pigments than activated carbon, and the decolorizing adsorbent material can be reused after activation and regeneration. For example, the decolorizing adsorbent material can be selected from Juxin Co. PACC-W activated carbon, URARAY Co. PW activated carbon, and U.S.A CABOT Co. DARCO® G-60 activated carbon.

In the S600 stripping step: stripping the second decolorizing product with steam at a temperature of 100° C. to 200°

C. for 2 hours to obtain the decolorized dioctyl terephthalate. The stripping step can be carried out under negative pressure to remove excess residual alcohol and some low boilers.

[Embodiment 1] Preparation of Dioctyl Terephthalate 400 g of recycled polyethylene terephthalate is mixed with 700 g of 2-ethylhexanol, and added with 0.71 g of catalyst tetraisopropyl titanate (TIPT), where the nitrogen reaction will gradually increase in temperature from 180° C. to 225° C. The reaction time is 2.5 hours, the reaction pressure is 1013 mbar for 1.5 hours, then −30 mbar for 1 hour to obtain the slurry of dioctyl terephthalate.

After the reaction, the acid value of the slurry of dioctyl terephthalate is 1 mg KOH/g, and is neutralized with alkali hydroxides solution to the acid value less than 0.07 mg KOH/g. Then, distillation is performed to reduce the alcohol content to below 300 ppm. After the reaction, the colorimetry of the dioctyl terephthalate is #200, and the colorimetry after the alkaline washing and neutralization step is #105.

[Embodiment 2-1] Redox Reaction Step 1.5 g of thiourea dioxide is mixed with 3 g of activated carbon, and added with 600 g of dioctyl terephthalate, to prepare a total amount of 1 L aqueous solution, which the aqueous solution is then stirred at 100° C. for 3 hours to be decolored. After the reaction, the aqueous solution is allowed to stand for 8 hours for separation of the layers, the liquid layer is filtered out of the liquid, and then after an appropriate amount of diatomite is suction filtered, the colorimetry of the unpurified dioctyl terephthalate will decrease from #105 to #61.

[Embodiment 2-2] Decolorization Step

Taking the unpurified dioctyl terephthalate treated in Example 2-1, 6 g of acid clay is added to prepare a total amount of 1 L aqueous solution, which the aqueous solution is then stirred at 100° C. for 1 hour to be decolored. After the liquid layer is filtered out of the liquid, and an appropriate amount of diatomite is suction filtered, the colorimetry of the unpurified dioctyl terephthalate will decrease from #60 to #25.

[Embodiment 3-1] Redox Reaction Step 6 g of hydrogen peroxide is mixed with 3 g of activated carbon, and added with 600 g of dioctyl terephthalate, to prepare a total amount of 1 L aqueous solution, which the aqueous solution is then stirred at 100° C. for 3 hours to be decolored. After the reaction, the aqueous solution is allowed to stand for 8 hours for separation of the layers, the liquid layer is filtered out of the liquid, and then after an appropriate amount of diatomite is suction filtered, the colorimetry of the unpurified dioctyl terephthalate will decrease from #105 to #42.

[Embodiment 3-2] Decolorization Step

Taking the unpurified dioctyl terephthalate treated in Example 3-1, 6 g of acid clay is added to prepare a total amount of 1 L aqueous solution, which the aqueous solution is then stirred at 100° C. for 1 hour to be decolored. After the liquid layer is filtered out of the liquid, and an appropriate amount of diatomite is suction filtered, the colorimetry of the unpurified dioctyl terephthalate will decrease from #42 to #25.

[Embodiment 4-1] Redox Reaction Step

Taking 1.5 g of sodium borohydride to prepare a total amount of 1 L sodium hydroxide aqueous solution, 600 g of dioctyl terephthalate is then added, and the mixture is stirred at 100° C. for 2 hours to be decolored. After the reaction, the mixture is allowed to stand for 8 hours for separation of the layers, the liquid layer is filtered out of the liquid, and after the appropriate amount of diatomite is suction filtered, the colorimetry of the unpurified dioctyl terephthalate will decrease from #105 to #60.

[Embodiment 4-2] Decolorization Step

Taking the unpurified dioctyl terephthalate treated in Example 4-1, 6 g of acid clay is added to prepare a total amount of 1 L aqueous solution, which the aqueous solution is then stirred at 100° C. for 1 hour to be decolored. The liquid layer is filtered out of the liquid, and after an appropriate amount of diatomite is suction filtered, the colorimetry of the unpurified dioctyl terephthalate will decrease from #60 to #25.

In conclusion, by virtue of "mixing the unpurified dioctyl terephthalate with a reducing agent and an adsorption medium, stirring for 1.5 to 3 hours, keeping for 6 to 10 hours, and filtering out the liquid, to obtain a first decolorizing product", "mixing the first decolorizing product with a decolorizing adsorbent material, stirring for 1.5 to 3 hours, keeping for 6 to 10 hours, and filtering out the liquid, to obtain a second decolorizing product", and "wherein the decolorizing adsorbent material has an acid value between 0.1 and 2 mg KOH/g, an relative humidity between 2 and 10%, and a fineness between 80 and 100 $cm^2/g$", the method for manufacturing and decolorizing dioctyl terephthalate of the present disclosure improves the decoloring effect of dioctyl terephthalate.

Furthermore, the decolorizing adsorbent material of the present disclosure belongs to a nano-level lattice adsorbent, which can adsorb finer substances and more pigments, so as to effectively improve the decolorization rate. Compared with only using the redox method or activated carbon adsorption, the decolorizing adsorbent material of the present disclosure can effectively reduce colorimetry. Furthermore, the manufacturing process of the dioctyl terephthalate of the present disclosure is simple and does not require additional equipment, which is beneficial to industrial applications thereof.

In addition, the present disclosure manufactures dioctyl terephthalate through recycled polyethylene terephthalate, which effectively utilizes polyethylene terephthalate plastic waste, meets the environmental protection requirements, and effectively reduces costs. Furthermore, the dioctyl phthalate plasticizer of the present disclosure has excellent compatibility with polyvinyl chloride, better processing performance, and good thermal aging stability.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A method for decolorizing dioctyl terephthalate, comprising:
providing an unpurified dioctyl terephthalate;
mixing the unpurified dioctyl terephthalate with a reducing agent and an adsorption medium, stirring for 1.5 to 3 hours, allowing to stand for 6 to 10 hours, and filtering out the liquid, to obtain a first decolorizing product; and
mixing the first decolorizing product with a decolorizing adsorbent material, stirring for 1.5 to 3 hours, keeping for 6 to 10 hours, and filtering out the liquid, to obtain a second decolorizing product;
wherein the decolorizing adsorbent material has an acid value between 0.1 and 2 mg KOH/g, a relative humidity between 2 and 10%, and a fineness between 80 and 100 $cm^2/g$.

2. The method for decolorizing dioctyl terephthalate according to claim 1, wherein, the reducing agent is at least one selected from the group consisting of thiourea dioxide aqueous solution, hydrogen peroxide, and an aqueous solution of sodium borohydride and sodium hydroxide.

3. The method for decolorizing dioctyl terephthalate according to claim 1, wherein the adsorption medium is at least one selected from the group consisting of activated carbon, zeolite, molecular sieve, diatomaceous earth, activated clay or activated alumina.

4. A method for manufacturing dioctyl terephthalate, comprising:
a transesterification step: mixing a recycled polyethylene terephthalate and a C3-C12 alcohol in a weight ratio of 1:0.8 to 1.5 with a catalyst, to obtain a slurry of dioctyl terephthalate; wherein, the slurry of dioctyl terephthalate includes an unpurified dioctyl terephthalate and an ethylene glycol;
an alkaline washing and neutralization step: neutralizing the unpurified dioctyl terephthalate with an alkali hydroxides solution;
a redox reaction step: mixing the washed and neutralized unpurified dioctyl terephthalate with a reducing agent and an adsorption medium, stirring for 1.5 to 3 hours, keeping for 6 to 10 hours, and filtering out the liquid, to obtain a first decolorizing product;
a decolorization step: mixing the first decolorizing product with a decolorizing adsorbent material, stirring for 1.5 to 3 hours, keeping for 6 to 10 hours, and filtering out the liquid, to obtain a second decolorizing product; and
a stripping step: stripping the second decolorizing product with steam at 100° C. to 200° C. for 2 hours to obtain a decolorized dioctyl terephthalate;
wherein, the decolorizing adsorbent material has an acid value between 0.1 and 2 mg KOH/g, a relative humidity between 2 and 10%, and a fineness between 80 and 100 $cm^2/g$.

5. The method for manufacturing dioctyl terephthalate according to claim 4, wherein the transesterification step is under a reaction pressure between −30 and 1013 mbar, a reaction temperature between 200 and 250° C., and a reaction time between 2 and 3 hours.

6. The method for manufacturing dioctyl terephthalate according to claim 4, wherein the C3-C12 alcohol is at least one selected from the group consisting of N-propanol, isopropanol, n-butanol, sec-butanol, tert-butanol, pentanol, hexanol, heptanol, octanol, isooctanol, 2-ethylhexanol, ethylene glycol monomethyl ether, ethylene glycol monoethyl ether and ethylene glycol monobutyl ether.

7. The method for manufacturing dioctyl terephthalate according to claim 4, wherein the catalyst is at least one selected from the group consisting of tetraisopropyl titanate, tetraisobutyl titanate, and tetra (2-ethylhexyl) titanate.

8. The method for manufacturing dioctyl terephthalate according to claim 4, wherein, the alkali hydroxides solution includes: 5 to 20 wt % hydroxide based on a total amount of the alkali hydroxides solution.

9. The method for manufacturing dioctyl terephthalate according to claim 4, wherein, the reducing agent is at least one selected from the group consisting of thiourea dioxide aqueous solution, hydrogen peroxide, and an aqueous solution of sodium borohydride and sodium hydroxide.

10. The method for manufacturing dioctyl terephthalate according to claim 4, wherein, the adsorption medium is at least one selected from the group consisting of activated carbon, zeolite, molecular sieve, diatomaceous earth, acid clay, activated clay or activated alumina.

* * * * *